United States Patent [19]
Gibbs, Jr. et al.

[11] Patent Number: 5,311,763
[45] Date of Patent: May 17, 1994

[54] METHOD AND APPARATUS FOR MEASURING BEARING FRICTION

[75] Inventors: Robert M. Gibbs, Jr., San Jose; Christopher L. Marquis, Milpitas; Bernard A. Messineo, San Jose, all of Calif.

[73] Assignee: Conner Peripherals, Inc., San Jose, Calif.

[21] Appl. No.: 843,893

[22] Filed: Feb. 27, 1992

[51] Int. Cl.$^5$ .......................................... G01N 19/02
[52] U.S. Cl. ...................................................... 73/9
[58] Field of Search ................... 73/9, 10, 118.1, 865.9

[56] References Cited
U.S. PATENT DOCUMENTS

| | | | |
|---|---|---|---|
| 2,760,366 | 8/1956 | Farmer | 73/9 |
| 2,867,114 | 1/1959 | Mims | 73/9 |
| 3,685,342 | 8/1972 | Gordon | 73/9 |
| 4,763,508 | 8/1988 | Buck | 73/9 |

Primary Examiner—Jerry W. Myracle
Attorney, Agent, or Firm—Fliesler, Dubb, Meyer & Lovejoy

[57] ABSTRACT

A method for testing rolling contact bearings, where each bearing has an inner race and an outer race. The method comprises: coupling the outer race of the bearing to a strain gauge; rotating the inner race of the bearing in a first direction and measuring the torque exerted on the outer race; and rotating the inner race of the bearing in a second direction and measuring the torque exerted on the outer race. In another aspect, the invention comprises an apparatus for testing bearings. The apparatus includes elements for rotating the inner race of the bearing; a strain gauge; elements for coupling the outer race of the bearing to a strain gauge; and elements, coupled to the strain gauge, for measuring the force applied to the strain gauge when the inner race is rotated.

24 Claims, 11 Drawing Sheets

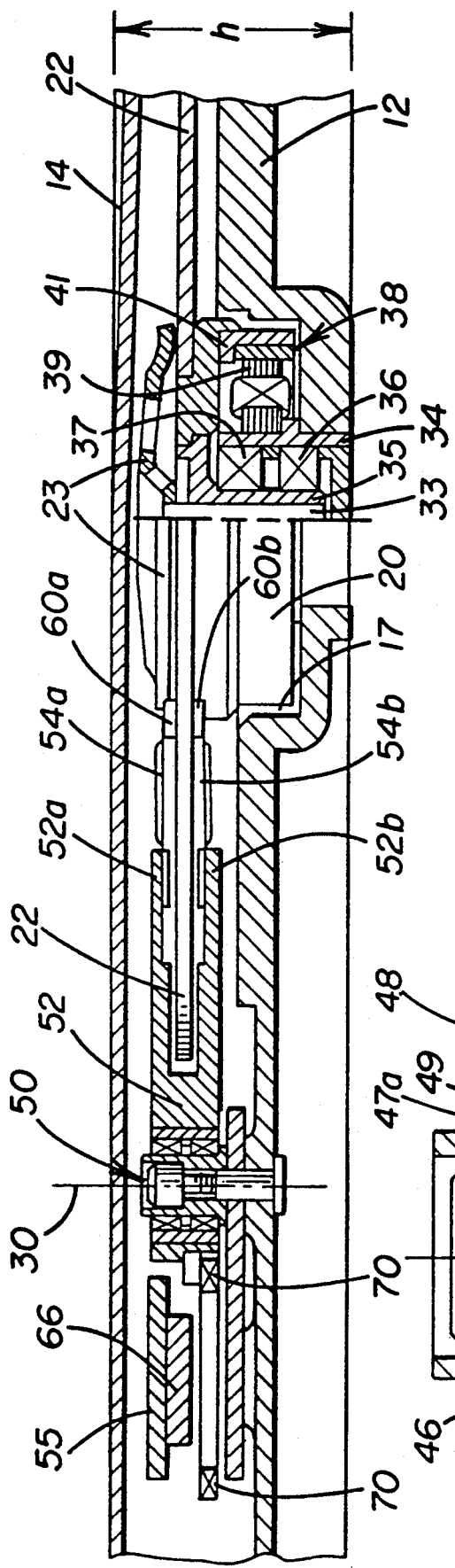
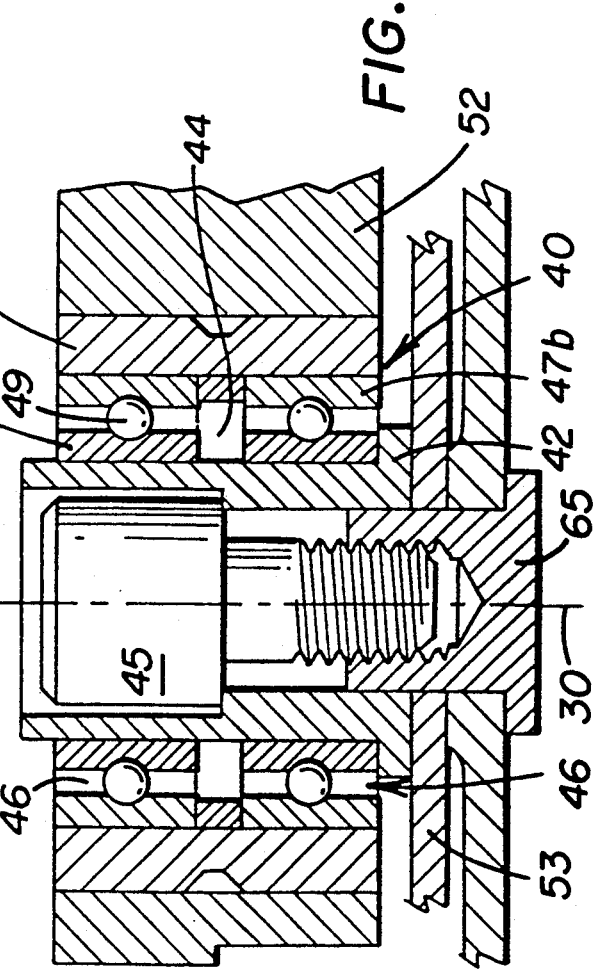
FIG. 11A
FIG. 11B

METHOD AND APPARATUS FOR MEASURING BEARING FRICTION

BACKGROUND OF THE INVENTION

1. Field of the Invention

The invention relates to a method and apparatus for evaluating the efficiency of rolling contact bearings which are used, for example, in disk drive data storage devices.

2. Description of the Related Art

Rolling contact bearings are utilized in numerous mechanical applications to transfer loads between rotating and stationary structures, (or two rotating structures), to permit free movement of rotating elements with minimal friction. Such bearings have a typical structure which is characterized by an inner ring or "race", an outer race, and rotating elements, such as balls or rollers, separating the inner and outer races. In addition, cages are typically used to separate the rotating elements from each other.

Rolling contact bearings are a key component of Winchester-type hard disk drive storage devices. An exemplary use of rolling contract bearings in such a drive is shown in FIGS. 11A–11B. FIGS. 11A and 11B are partial, cross-sectional views of a typical Winchester-type hard disk drive, wherein data is stored on a disk 22 by read/write heads 60A, 60B, positioned with respect to a disk by a rotary-type actuator assembly. The rotary-type actuator includes: actuator arm 52 having first and second subarms 52A, 52B, for supporting load beams 54A, 54B, respectively, on which read/write heads 60A, 60B, are mounted; a bearing assembly 40; and a voice coil motor assembly, including coil 70 and magnet 66.

The disk drive shown incorporates two bearing assemblies each having two rotary bearings translating loads between the stationary disk housing and rotary elements. A first bearing assembly is utilized to allow actuator body 52 to rotate about stationary mounting post 42, secured in base 12 on the disk drives. This first bearing assembly comprises two bearings 46 mounted in a bearing cartridge 40. A second bearing structure, comprising bearings 36 and 37, is used for supporting a spindle motor and hub assembly to allow for rotation of disk 22, shaft 35, and hub 41 with respect to base 12.

As shown in FIG. 11B, actuator bearing cartridge 40 is comprised of two single row radial bearings 46, each having an inner race 47A and outer race 47B, separated by balls 49. Bearing cartridge 40, includes an outer casing 48 in which bearings 46 are preloaded and separated by a spacer 44. Preloading of bearings 46 in this manner facilitates final assembly of the actuator in the disk drive. Bearings 36 and 37 may also comprise single row radial bearings (not detailed) which separate mounting shelf 34 for the disk 22 from the base 12. In normal drive operation, actuator 52 positions head 60A, 60B about a rotational axis 30 passing through the center of hex screw 45, used to secure mounting post 42 to base 12. Actuator 52 positions read/write heads 60A, 60B at individual tracks on each surface of disk 22 under the direction of control electronics to read and write data therefrom. The force required to move actuator 52 is provided by a voice coil motor comprising magnet 66 and coil 70. Magnet 66 is arranged so that a current in coil 70, in relation to the magnetic field generated by magnet 66, controls positioning of actuator 52 around rotational axis 30. Typically the density of individual tracks on disk 22 is on the order of 2,000 tracks per inch. Thus, the accuracy required for positioning actuator 52 is extremely high. In addition, such disk drives are designed and manufactured to meet certain predetermined performance specifications, including, for example, data access times and actuator seek times which are, in part, related to the efficiency with which actuator 52 may be positioned. Thus, the running friction between the inner and outer rates of bearings 46 comprising cartridge 40 affects the overall drive performance specifications for the drive. Hence, it is important that the bearing cartridge 40 operate within the required design specifications to ensure the actuator's movement relative to support post 42.

Furthermore, seek times are related to spindle motor efficiency and the speed at which disk 22 is rotated about shaft 35. Thus, operation of bearings 36 and 37 is also crucial to the drive's ability to perform to specifications.

Generally, the rolling contact bearings utilized in disk drives are supplied to the disk drive manufacturer by an outside vendor and are represented as having the ability to operate within the drive manufacturer's defined specifications. There is therefore little opportunity for the drive manufacturer to implement quality control over bearing manufacture. A percentage of all the bearings supplied to the disk drive manufacturer do not meet the defined specifications and have a unacceptably high degree of running friction. Running friction is defined as the friction between the inner and outer races of the bearing, measurable as a resistance torque.

As a means for ensuring quality in the manufactured disk drive, systems for testing the running friction in such bearings are available. One such system manufactured by Vibrac Corporation, is available for testing the running friction between the inner and out races of one rolling contact bearing, such as those shown in FIGS. 11A and 11B. However, such conventional systems are generally extremely large and cumbersome, and require a large amount of floor space dedicated for the use of the device. Such devices are not suitable for easy movement to a number of locations. Further, conventional devices are currently limited to one bearing test station per device, thus allowing only one separate bearing to be tested at any one particular time by the testing unit.

Thus, an object of the invention is to provide an improved method and apparatus for testing rolling contact bearings.

A further object of the invention is to provide a method and apparatus for testing rolling contact bearings which has a reduced size and ease of portability.

Another object of the invention is to provide a system for testing rolling contact bearings which may include up to eight separate bearing testing stations coupled to a single control means.

A further object of the invention is to provide a apparatus and method for testing rolling contact bearings which are utilized in disk drives, and specifically, a system which may be adapted to test various different sizes of rolling contact bearings.

Yet another object of the invention is to provide a system for testing rolling contact bearings which is adaptable for testing assembled bearing cartridges utilized in disk drive storage devices.

SUMMARY OF THE INVENTION

These and other objects of the invention are provided in a method and apparatus for testing rolling contact bearings. In one aspect, the invention comprises a method for testing rolling contact bearings, where each bearing has an inner race and an outer race. The method comprises: coupling the outer race of the bearing to a strain gauge; rotating the inner race of the bearing in a first direction and measuring the torque exerted on the outer race; and rotating the inner race of the bearing in a second direction and measuring the torque exerted on the outer race. In another aspect, the invention comprises an apparatus for testing bearings. The apparatus includes means for rotating the inner race of the bearing; a strain gauge; means for coupling the outer race of the bearing to the strain gauge; and means, coupled to the strain gauge, for measuring the force applied to said strain gauge when said inner race is rotated.

BRIEF DESCRIPTION OF THE DRAWINGS

The invention will be described with respect to particular embodiments thereof. Other objects, features, and advantages of the invention will be apparent with reference to the specification and the drawings, in which:

FIGS. 11A and 11B are side views of an exemplary disk drive illustrating the use of rolling contact bearings therein which may be tested in accordance with the apparatus and method of the present invention.

DESCRIPTION OF THE PREFERRED EMBODIMENT

The bearing testing system of the present invention includes a method and apparatus which translates the running friction between the inner and outer races of a rolling contact bearing into a measurable electrical signal utilizing a strain gauge coupled in a full Wheatstone-bridge arrangement. The running friction of the bearing under test is determined by measuring the resulting friction from rotation of the inner race of the bearing in a clockwise and counterclockwise direction, with the magnitude of the friction in each direction being measured, and compared to a maximum allowable value.

Figure 1:
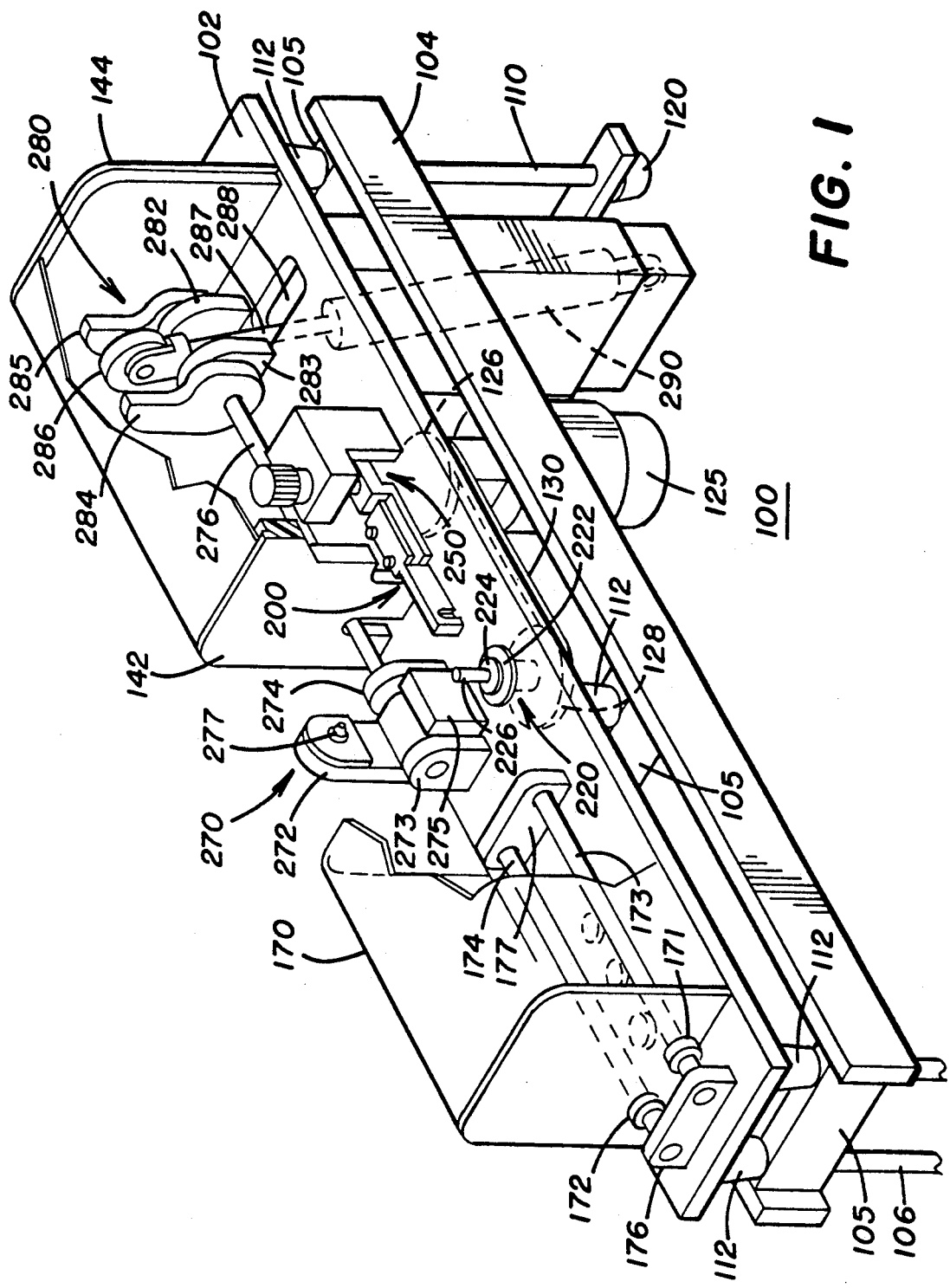
FIG. 1 is a perspective view of an apparatus for testing bearings in accordance with the method and apparatus of the present invention.
Figure 2:
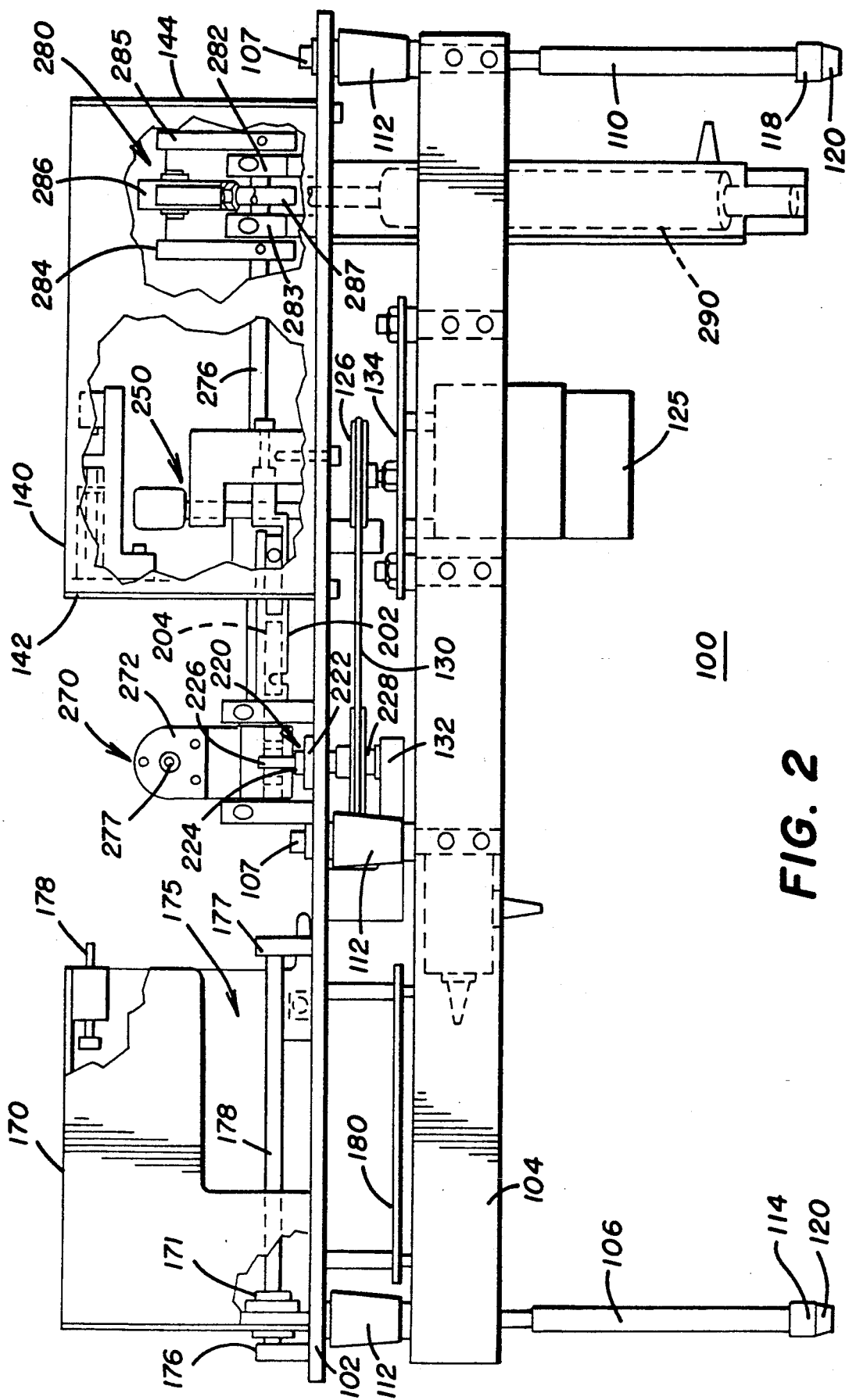
FIG. 2 is a side view of the apparatus for testing bearings in accordance with the method and apparatus of the present invention.

FIGS. 1 and 2 show an apparatus for testing radial bearings in accordance with the method and apparatus of the present invention. Apparatus 100 is portable, and may be utilized in a clean room environment in either a multi-station system, with up to eight testers 100 coupled to and controlled by one personal computer, or in a single tester desk top configuration. Bearing friction tester 100 is automated to provide for measurement between the running friction levels between the shaft or "inner race" and the "outer races" of radial bearings. Once properly configured for testing purposes, the apparatus requires minimal involvement from the user. Loose bearings, cartridge bearings, or disk drive actuator assemblies can be tested on this fixture with few modifications. The testing system, described herein, provides for both data output and hard copy results of numerous statistical data on the bearing under test, including average friction, maximum and minimum friction values, standard deviation, and friction range.

Figure 10:
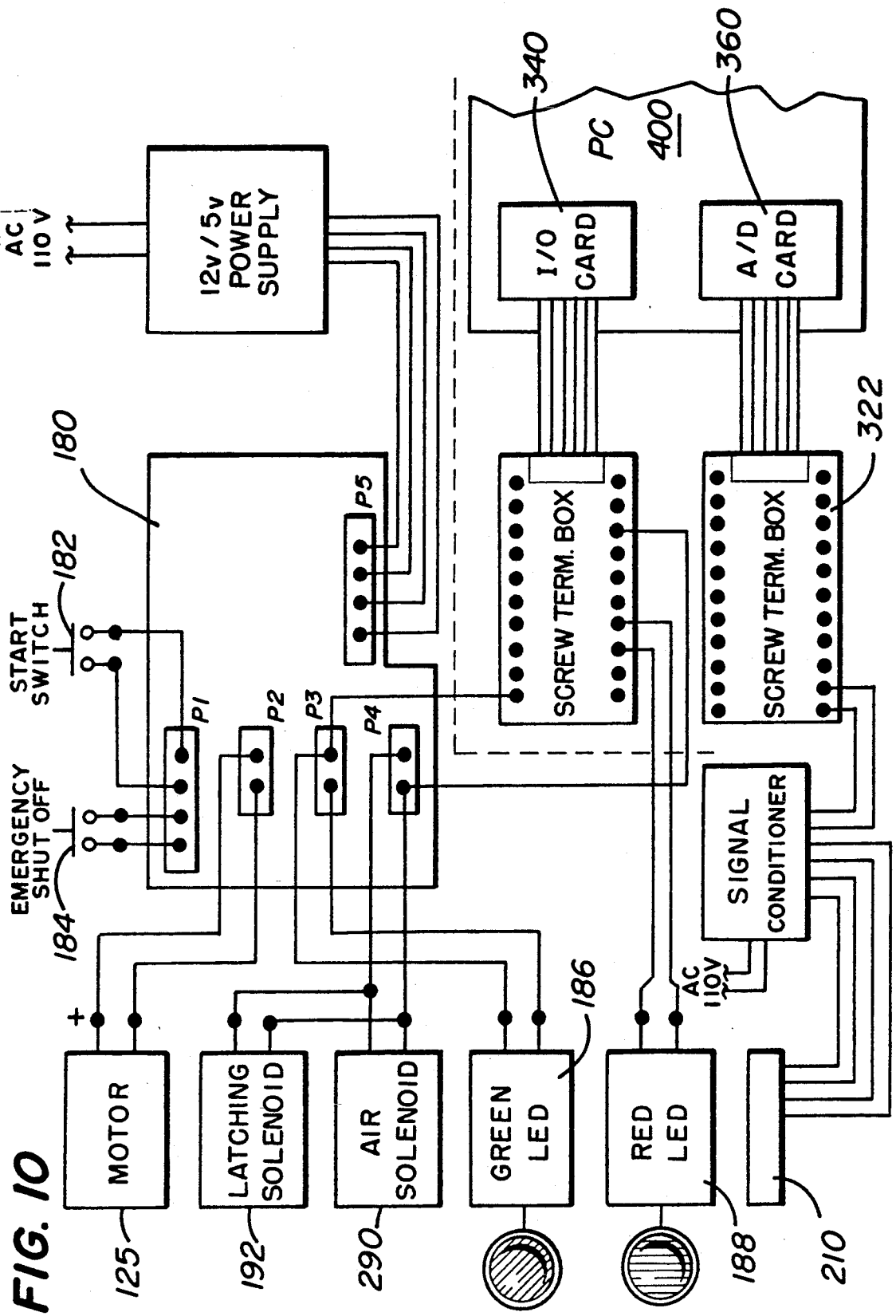
FIG. 10 is a block wiring diagram depicting one embodiment for coupling the outputs of the timing electronics to the various components of the apparatus and the control means, and one embodiment for coupling the strain gauge to the control means of the present invention.

Bearing friction tester 100 operates by utilizing a load beam/strain gauge assembly to convert the mechanical force generated between the inner and outer races of the bearing when the bearing is rotated into an electrical potential via a full resistor bridge arrangement. As shown in FIG. 10, a low level output signal from the strain gauge is fed into a signal conditioner where amplification of the signal takes place. The amplified signal is then fed to an analog acquisition card within a personal computer. With the appropriate data acquisition software, the resulting signal is analyzed, manipulated, and graphically displayed to the user. Hard copies of the data may also be obtained.

As shown in FIGS. 1 and 2, the major components of the bearing friction tester 100 of the present invention include: a housing, comprising base plate 102, frame 104, and legs 106, and 110; spindle 220, for mounting a bearing or bearing cartridge under test; a bearing clamp assembly 270, for securing the bearing or bearing cartridge under test on spindle 220; load beam/strain gauge assembly 200, for positioning the strain gauge of apparatus 100; motor 125, for rotating spindle 220; slidable cover 170, for securing the testing region during the test sequence; and clamp counterweight assembly 280, for rotating clamp assembly 270 over spindle 220. A printed circuit board (PCB) 180, including the timing electronics for running the various electromechanical components of the apparatus is mounted to base plate 102. Personal Computer (PC) 400 is an Intel 80386 microprocessor based personal computer and acts as the control means for all testing functions (FIG. 10).

Figure 8:
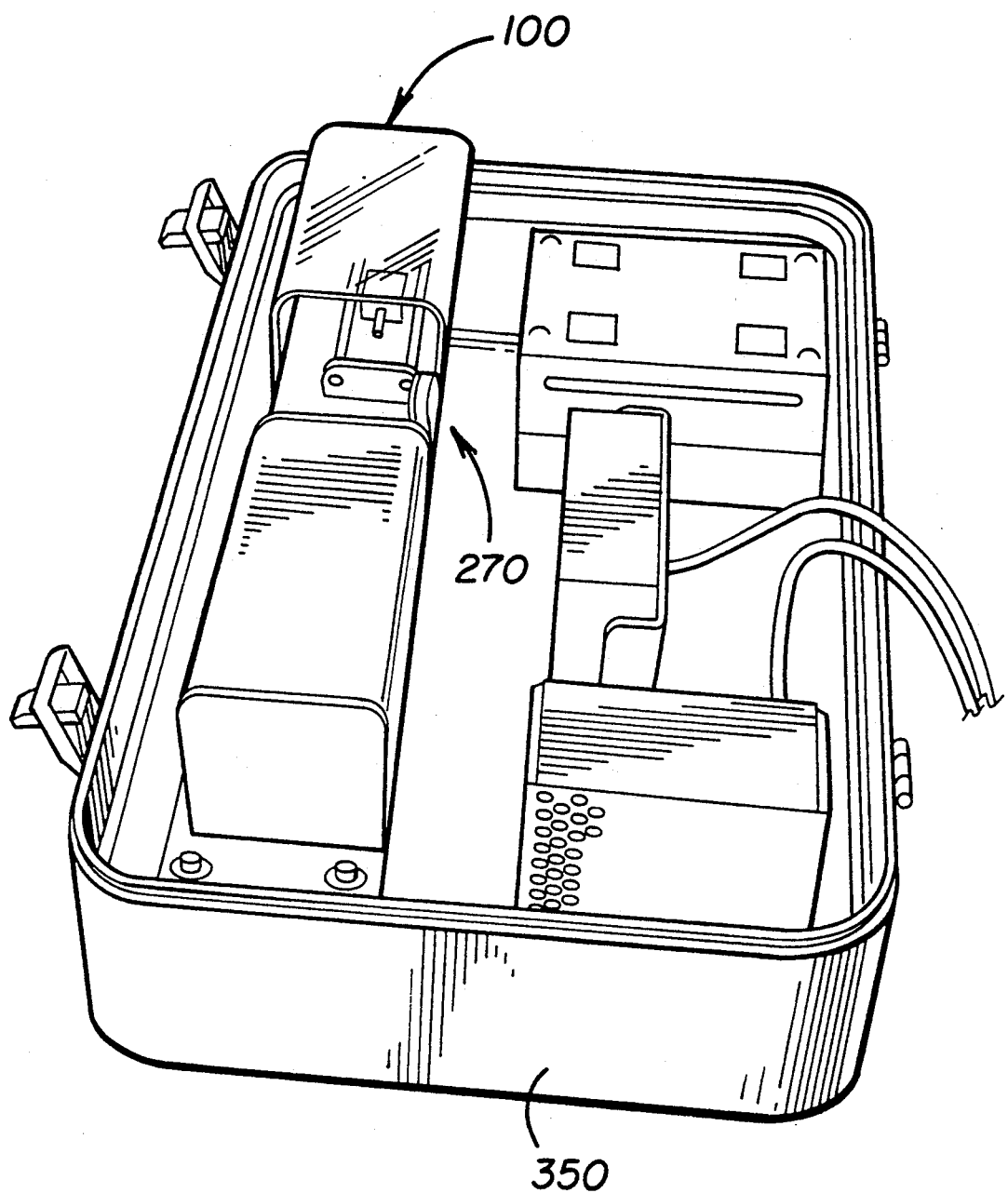
FIG. 8 is a perspective view of a single station bearing test apparatus of the present invention in a portable casing configuration.

Base plate 102 is supported on frame 104 by a plurality of rubber bushings 112 which surround the steel mounting posts (not shown) coupled to cross beams 105 and secured to base plate 102 by lock caps 107. Legs 106, and 110 are coupled to feet 114, and 118, which support bearing friction tester 100 on rubber bushings 120. The use of rubber bushings 112, 120 allows the mechanical components of the bearing friction tester, described above, to be isolated from vibrations or physical shocks transmitted thereto from the support surface, which may comprise a work table, portable case, or an integrated structure for supporting a number of bearing testers. The sensitivity of strain gauge assembly 200 used in bearing friction test apparatus 100 is such that vibrations transmitted from the ambient external environment to assembly 200 would denigrate the test results. The use of rubber bushings 112 and 120 tends to eliminate such interference. The design of the housing is suitable to provide for testing operations in a transportable arrangement, as shown in FIG. 8. FIG. 8 shows the lower portion of a transport case 350, having a depth sufficient to accommodate tester 100 so that base plate 102 is flush with the upper surface of the case edge. This allows for the upper portion of case 350 to be removed and easy setup of the tester.

Spindle 220 includes a base 222, inner flange 224, and central post 226 on which a bearing or bearing cartridge, such as bearing cartridge 40 shown in FIG. 11B, may be placed. It should be understood by those skilled in the art that the configuration of spindle 220 may be adapted for different types of bearings and need not be limited to the specific structure shown in FIGS. 1 and 2. For purposes of discussion, operation of bearing tester 100 will be described with reference to bearing cartridge 40.

Figure 3:
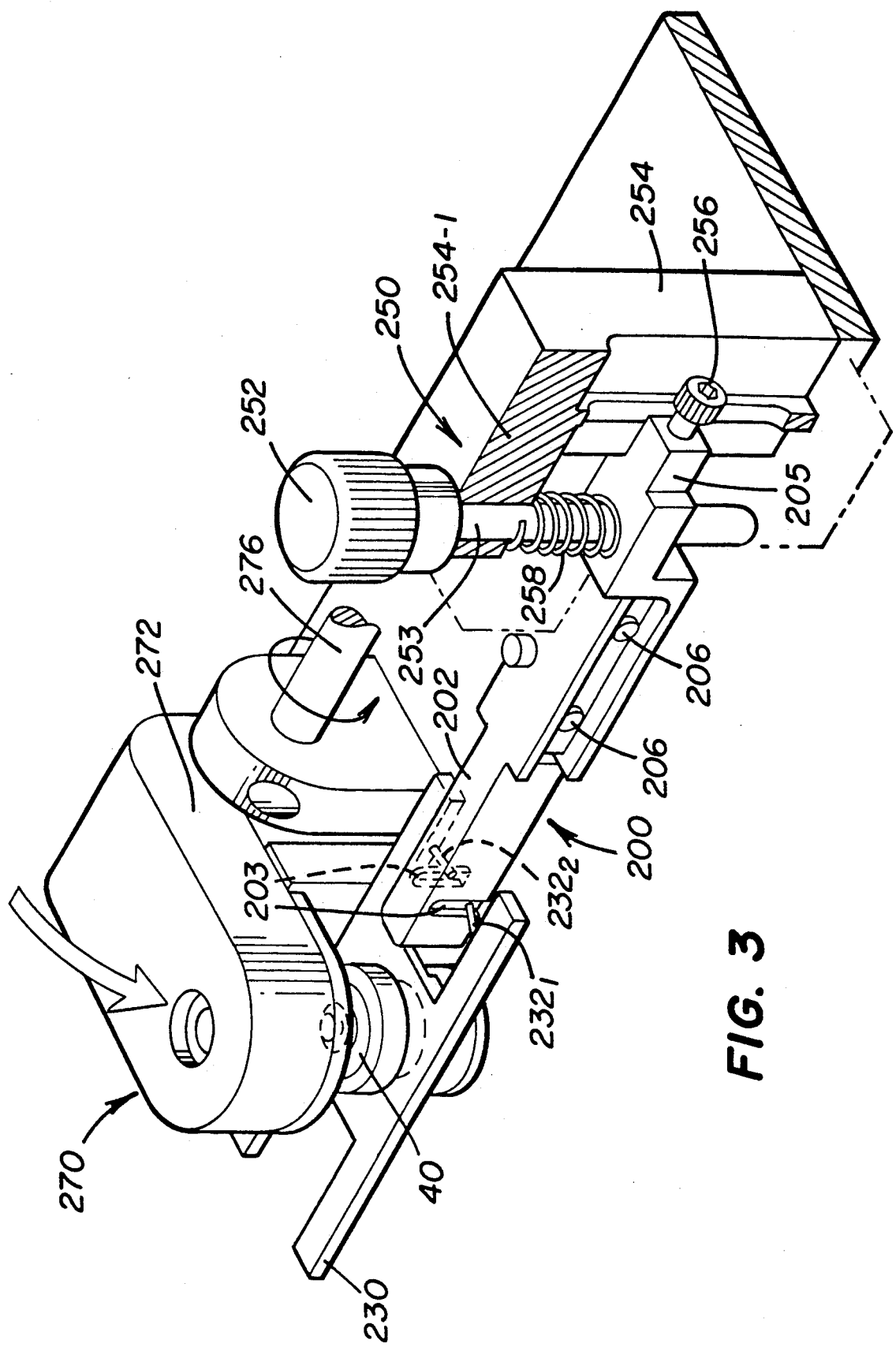
FIG. 3 is an enlarged perspective view of the bearing clamp, and strain gauge mounting and bearing test fixture assembly of the apparatus of the present invention.
Figure 4:
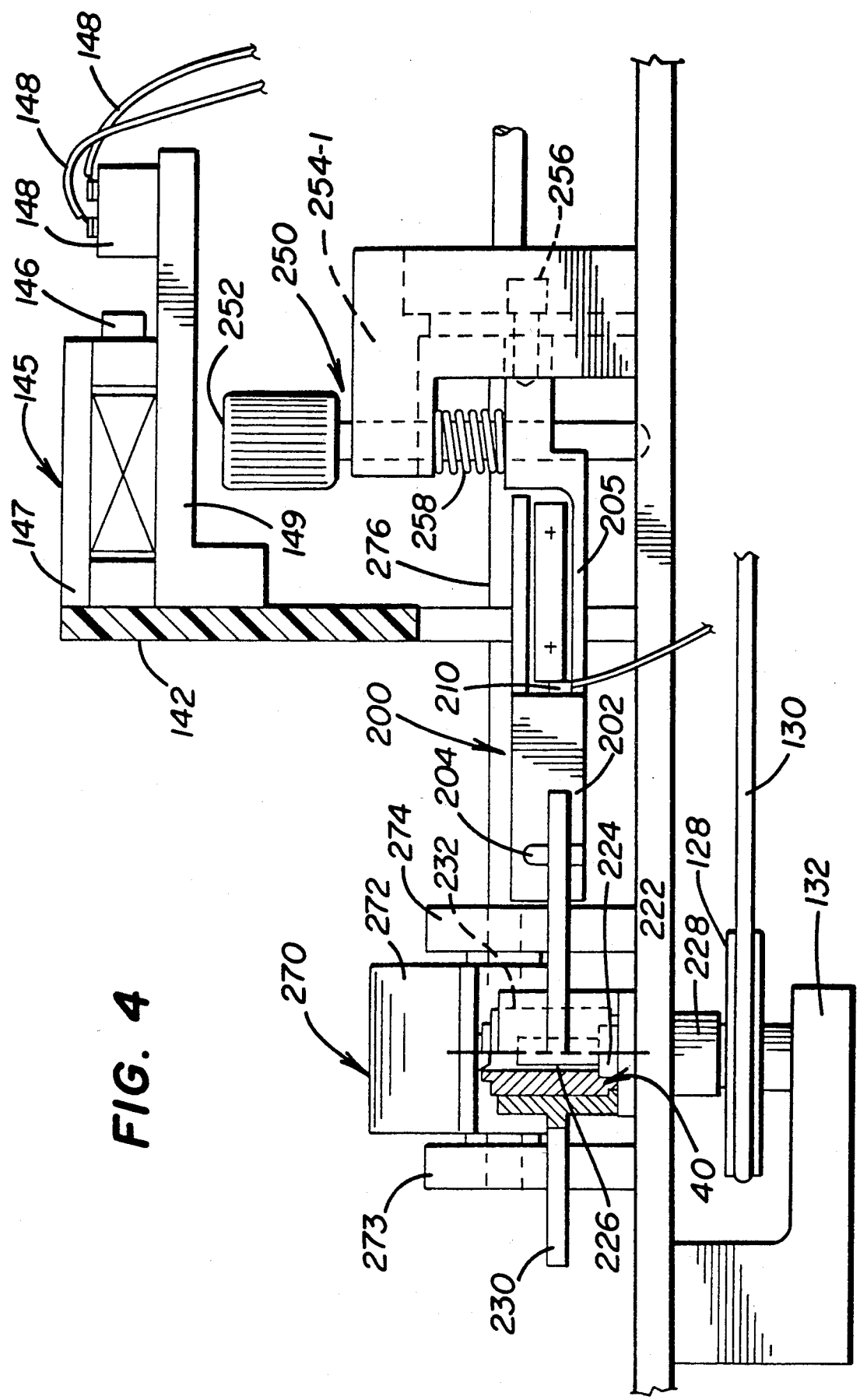
FIG. 4 is an enlarged, front side view of the bearing clamp, and strain gauge mounting and bearing test fixture assembly of the apparatus of the present invention.

As shown in FIG. 4, bearing cartridge 40 is mounted onto spindle 222 such that the post 226 of spindle 220 engages the central cylindrical bore defined by the inner races of the bearings structure therein. Flange 224 of spindle 220 supports the bearing cartridge under test and engages the inner races of the bearings in cartridge 40. Spindle 220 is coupled by shaft 228 to mounting bracket 132 (FIG. 4) which supports shaft 228 and pulley 128, used for transmitting the rotation motor 125 to spindle 220 and, hence, to the inner races of the bearings under test. As shown in FIGS. 3 and 4, bearing holder 230, having a cylindrical inner bore 232, is utilized to test bearing cartridge 40. Bore 232 snugly engages the outer sleeve 48 of bearing cartridge 40 when cartridge 40 is mounted on spindle 220. As will be explained in further detail below, bearing holder 230 allows the rotational force transmitted to the outer races of the bearings comprising bearing cartridge 40 from the inner races thereof to be transmitted to strain gauge assembly 200.

Motor 125 (FIGS. 1 and 2) is mounted to bearing friction tester 100 by support bracket 134 secured to cross beams 105. The output shaft of motor 125 is coupled to pulley 126. A rubber chain 130 couples gear 126 and gear 128 to translate the rotation of motor 125 to spindle 220. A motor suitable for use in apparatus 100 is Model No. P/N 713-982922, manufactured by Minarik Motor Company, requiring a 12 Volt DC input, providing a no load rpm of 5.8 revolutions per minute with a running torque, at 4.6 revolutions per minute, of 20 inch-lb. The sizing of pulley 126 and pulley 128, and their translation of the rotation of motor 125 to spindle 220 yields an rpm rate of 5.8 for spindle 220.

Figure 5:
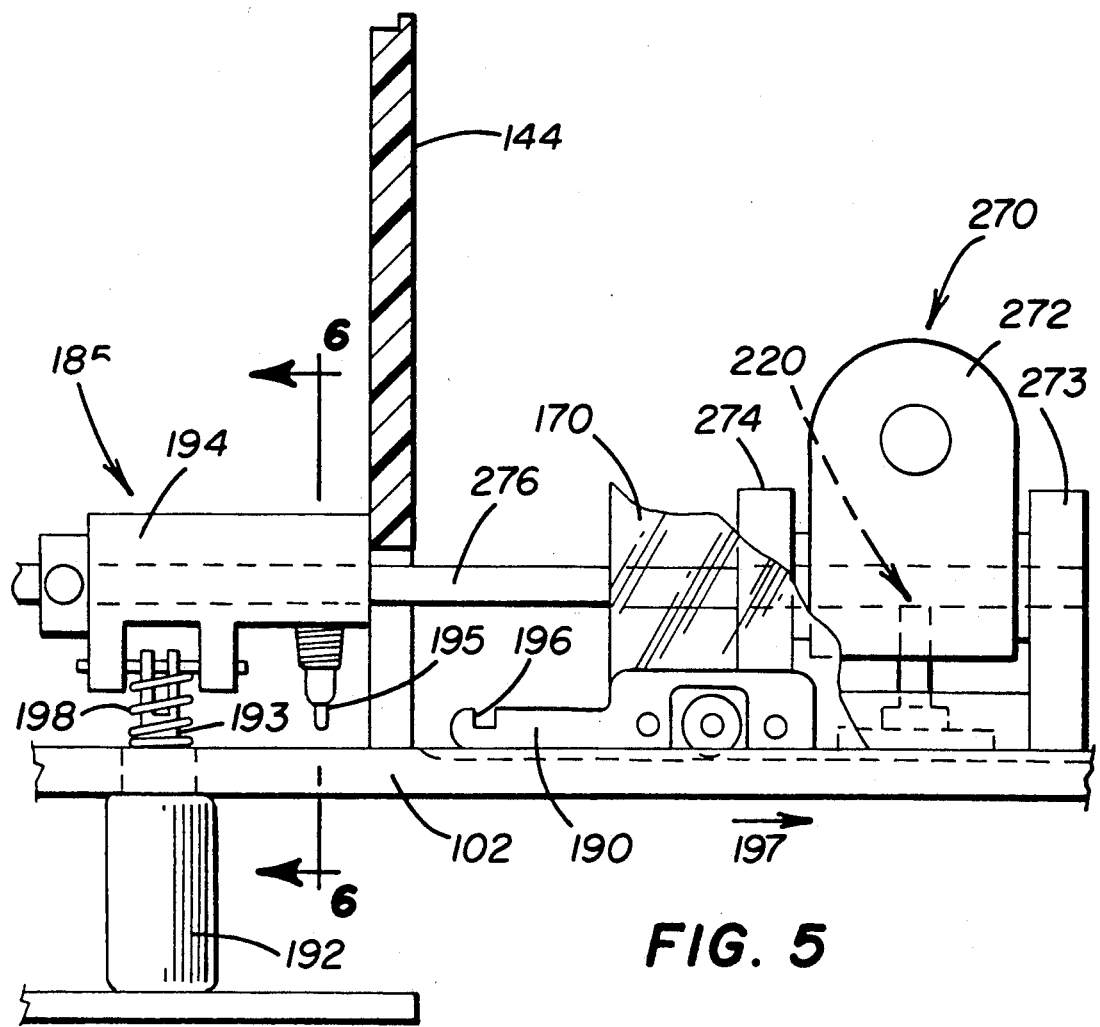
FIG. 5 is an enlarged, rear side view of the bearing clamp and cover latch assembly of the apparatus of the present invention.

As shown in FIG. 3, bearing clamp assembly 270 is utilized to hold bearing cartridge 40 and bearing holder 230 on spindle 220 during the testing sequence. Bearing clamp assembly 270 comprises clamp arm 272, mounting shoulders 273, 274, stop block 275 and shaft 276. Bearing clamp arm 272 is secured to shaft 276 to rotate therewith approximately 90° to hold bearing holder 230 and bearing cartridge 40 on spindle 220. Shoulders 273,274 support shaft 276 and arm 272 for rotation. Stop block 275 ensures that the rotational movement of bearing clamp arm 272 does not exceed 90° with respect to its release position (FIGS. 1, 2, 5). With reference to FIG. 3, clamp arm 272 is shown in its rotated, clamped position over bearing cartridge assembly 40 mounted on spindle 220. Bearing arm 272 rotates with shaft 276; rotation is controlled by air solenoid 290 and counterweight assembly 280. Clamping cartridge 40 ensures that cartridge 40 is stable during the testing operation. Arm 272 includes a conical finger 277 which engages the upper portion of the cylindrical bore defined by the inner races 47a of bearings 46 comprising cartridge 40. A bearing assembly (not shown) within arm 272 allows finger 277 to rotate with inner races 47a of cartridge 40 when spindle 220 rotates during the test sequence. However, any resistance attributable to the contact of inner race 47a with finger 277 on the test sequence is negligible since finger 277 does not contact the outer races of the bearing under test.

As shown in FIGS. 1 and 2, pivot assembly 280 is coupled to a second end of shaft 276 and, in conjunction with solenoid 290, operates to rotate shaft 276 and clamp arm 272 under the control of the timing circuitry on printed circuit board 180. Assembly 280 comprises mounting members 282, 283, secured to base plate 102, coupling arm 286, and pivot members 284, 285, coupled to shaft 276. Coupling arm 286 has one end coupled to shaft 276 and an opposite end coupled to output shaft 287 of air solenoid 290. Coupling arm 286, and pivot members 284,285 are preferably machined from a single piece of steel and are joined by a crossbeam (not shown) thereby forming a single piece part. Output shaft 287 of air solenoid 290 extends through slot 288, provided in base plate 102, which allows horizontal movement of shaft 287 in conjunction with arm 286 when shaft 287 is extended and retracted. As will be generally understood, coupling lever 286 (and pivot members 284,285) rotate responsive to the extension and retraction of shaft 276 by air solenoid 290. As shown in FIG. 1, when output arm 287 is extended, clamp arm 272 is in the cartridge release position. When output arm 287 is retracted, coupling lever 286 is rotated approximately 90° pulling clamp arm 272 into engagement with a bearing cartridge 40, as shown in FIGS. 3 and 4.

Detection of the running friction between the inner and outer races of the bearings in bearing cartridge 40, (or of an individual bearing under test), is accomplished by translating the frictional force between the inner and outer races of the bearing to bearing holder 230 and, in turn, to a strain gauge mounted in strain gauge assembly 200. An ideal bearing would exhibit minimal resistance between the inner and outer races when one source is rotated. In reality, the frictional force between the bearings is measurable as the torque exerted on bearing holder 230 resulting from the rotation of spindle 220 and inner races 47a of bearings 46 in cartridge 40.

As shown in FIGS. 2 and 3, load beam/strain gauge assembly 200 comprises a mounting arm 202 which houses strain gauge 210 and load beam 204 therein. A strain gauge suitable for use in apparatus 100 of the present invention is manufactured by Measurements Group, Inc. Part No. TK-09-125PC-350, having a resistance of 350 ohms, a maximum strain of ±1600 microstrain, and an accuracy of 0.2–0.5% full scale Beam assembly 202 may be manufactured by Engineering Specifics, Inc. and is coupled to mounting beam 205 by screws 207. A transducer load beam 204 of beryllium copper with a thickness of 0.010 inches is provided within assembly 202. Conventionally, strain gauges are provided as variable resistance elements wired in a Wheatstone bridge arrangement. In the instant embodiment, gauge 210 is a full Wheatstone bridge arrangement, with the variation in the gauge being translated to a microvoltage analog output signal for use by a personal computer with data acquisition software via a signal conditioner. In this embodiment, the Wheatstone bridge arrangement is provided on load beam 204. As shown in FIG. 10, the voltage output of the Wheatstone bridge is amplified by a signal conditioner 320, such as Daytronic Model 3170, to which strain gauge 210 is coupled. Conditioner 320 provides an analog output to an A/D data acquisition card 360 in personal computer 400, which may be utilized as the control means for up to 8 bearing testers 100. Each conditioner 320 is associated with one respective tester 100, and is coupled to A/D card 360 via a screw terminal box 322; box 322 is capable of coupling up to 8 testers 100 to the personal computer. A/D data acquisition card 360 may comprise a 16-channel high speed A/D interface such as Model DAS-16 manufactured by Keithley Metrabyte Corp., Taunton, Mass.

As shown in FIG. 2, transducer load beam 204 is positioned in arm 202, with gauge 210 coupled to one end of load beam 204, and load beam 204 coupled by screws 206 to beam 205. Arm 202 includes slots 203 arranged on opposing sides thereof to allow pins 232 on bearing holder 230 to engage transducer load beam 204, thereby transmitting the torque on bearing friction holder 230 to strain gauge 210. Strain gauge mounting assembly 200 is supported by strain gauge mounting/adjustment assembly 250. Mounting/adjustment assembly 250 includes mounting beam 205 on which beam assembly arm 202 is mounted. Screws 206 secure assembly arm 202 to mounting/adjustment arm 205. Mounting-/adjustment assembly 250 includes adjustment knob 252 coupled to threaded screw 253, mounted to block 254, having coil spring 258 positioned between upper portion 254-1 of block 254 and mounting beam assembly 200.

As will be explained in further detail below, in operation, bearing holder 230 is placed around bearing cartridge 40 so that the outer race of a particular bearing is essentially in contact therewith, and any force exerted on such outer races is reflected in bearing holder 230. As will be generally understood, once the inner race of the bearing is driven to rotation by motor 125, for example, in the clockwise direction, the rotational friction between the inner and outer races of the bearings will cause bearing holder 230 and specifically pin $232_2$ to rotate in the same direction such that pin $232_2$ contacts transducer load beam 204 causing a force indicative of the resistance torque to be exerted on substrate 204 and strain gauge 210. Consequently, the voltage of the full Wheatstone bridge will vary in proportion to the linear force exerted thereon by bearing holder 230. The output of the bridge is provided to compute 330. The control software therein registers the running friction of the bearing, first when the bearing is rotated in a clockwise direction, and thereafter when the bearing is rotated in a counterclockwise direction under the direction of the timing electronics on board 180.

In order to assure the accuracy of strain gauge 210, the strain gauge assembly 200 must be adjusted to ensure load beam 204 is at an accurate height, centered with respect to the contact points of pins $231_1$, $232_2$. Adjustment knob 252 and screw 253 are secured in place by a hex lock nut 256. In order to adjust load beam 204 and strain gauge 210, hex nut 256 is loosened and arm 202 removed, exposing load beam 204. Load beam 204 is thereafter lowered to a position adjacent base plate 102 and the respective height adjusted to accurately center load beam 204 with respect to pins 232.

As shown in FIGS. 1 and 2, a cover plate 140 is provided to encase adjustment assembly 250, pivot assembly 280, cover latch assembly 185 and cover switch assembly 145. Test station cover 170 encases disk clamp 270, bearing casing 40 and strain gauge assembly 200 during each testing sequence to ensure that no physical contact between the system operator or external environment and the sensitive components of the testing station occurs during the testing sequence. Cover 170 is formed of clear or semi-clear plastic, and is mounted by linear bearings 172, 171 on guide rails 173, 174 secured to housing base plate 174 by mounting hubs 176, 177. Cover 170 includes window 175 to accommodate the larger size of actuator adapter 300, shown in FIGS. 7A and 7B, and described further below. Because of the size of actuator adapter 300 when bearing cartridge 40 is secured in actuator body 52 and body 52 is provided in adapter 300 on spindle 220, window 175 is necessary to allow freedom of movement for actuator adapter 300 during the test sequence.

A cover switch assembly 145 ensures that cover 170 is closed during the testing operation. Cover 170 includes pin 178 mounted to the upper portion thereof, which engages finger 146, forcing pin 146 into contact with switch 148. Finger 146, shown in a retracted position in FIG. 4, is provided in housing 147 and, when engaged by pin 178 upon closure cover 170, forces finger 146 into contact with switch 148 mounted on bracket 149. Switch 148 is coupled to personal computer 400 controlling test apparatus 100 by leads $148_1$ and $148_2$. Switch 148 acts as a safety mechanism to prevent the test operation from proceeding in the event cover 170 is not closed, protecting spindle 220, bearing holder 230, and spindle clamp 270.

Figure 6:
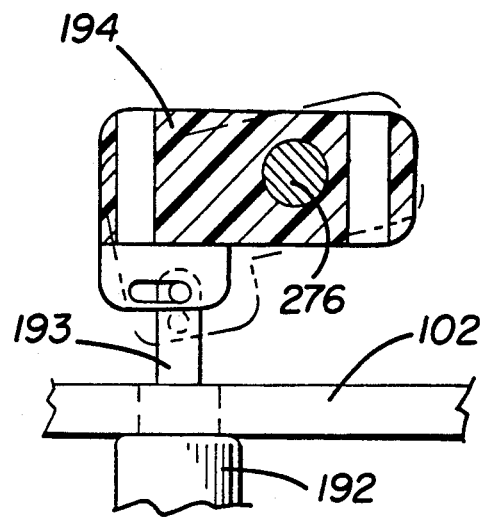
FIG. 6 is a view along line 6—6 in FIG. 5 showing the rotational latching movement of the latch body and solenoid of the cover latch assembly of the testing apparatus of the present invention.

As shown in FIGS. 5 and 6, cover 170 is latched in a closed position by latch assembly 185 which allows cover 170 to be automatically released by the control means. Notched latch arm 190 is coupled to cover 170 adjacent bearing friction tester housing base plate 102. Latch assembly 185 includes solenoid 192 having an output shaft 193 fastened to latch pivot 194 coupled to shaft 276. Pivot 194 includes a latch pin 195 for engaging latch arm notch 196 when cover 170 is moved into a closed position. To secure cover 170, pin 195 drops to engage notch 196 in notched arm 190, thereby retaining the cover 170 in a closed position. Latch pivot 194 pivots under the control of solenoid 192, which is coupled to the timing electronics in PCB 180, (as shown in FIG. 10), to allow the timing electronics to activate solenoid 192 to retract output shaft 193, thereby rotating pivot 194 about shaft 276, to lower pin 195 to engage latch arm 196, or to extend shaft 193 thereby raising pin 195 to unlatch cover 170. Spring 198 is provided about output shaft 193 to provide a rapid extension of shaft 193 and rotation of pivot 194. Cover 170 may be spring-loaded (not shown) to allow the cover to retract in a direction of arrow 197 away from wall 142 to indicate to the operator that the testing procedure has completed and that it is safe to remove the bearing cartridge 40 from the testing apparatus.

The aforementioned major electromechanical components of bearing tester 100 operate in conjunction with computer 400 to test rolling contact bearings in the following manner. Again, it should be noted that the bearing friction tester 100 of the present invention will be described with reference to its testing of rolling friction bearings in a bearing cartridge, such as bearing cartridge 40. It should be understood by those skilled in the art that bearing tester 100 may be modified to accommodate different types of rolling contact bearing arrangements.

Bearing cartridge 40 is first placed in bearing holder 230 and cartridge 40 and holder 230, are placed on spindle 220. As shown in FIG. 3, slots 203 are provided in arm 202 so that pins $232_1$ and $232_2$ may be positioned adjacent load beam 204 of strain gauge 210. Once bearing holder 230 and cartridge 40 are in place, cover 170 is slid toward wall 142 and pin 178 thereon engages switch 145, initiating a start signal to the timing electronics located on PCB 180, and described in further detail below.

The general operation of the control software present in PC 400 in conjunction with the timing electronics will be hereafter described with respect to the test control functions accomplished thereby. Specific aspects of the control software means utilized to accomplish those functions are detailed below therefore.

Air solenoid 290 is first activated to rotate arm 286 and clamp arm assembly 270 and holder 277 into contact with the inner races of bearing cartridge 40. Start switch 182, shown in FIG. 10, may be activated by switch 145 and triggered by the closing of cover 170 under the control of computer 400. Alternatively, a manual start button may be utilized to initiate the start sequence once bearing cartridge 40 is placed on spindle 220. All test operations are delayed for approximately 1.5 seconds while the clamp rotates about shaft 276. Once the 1.5 second delay is completed, motor 125 is driven to rotate spindle 220 in a clockwise direction for approximately 30 seconds. This allows the balls in each particular rolling contact bearing to make approximately one 360° revolution about the inner race. During this time, computer 400 gathers data input from the strain gauge responsive to the force applied to load beam 204 by pin $231_1$. At the completion of the 30 second duration, the motor stops, and the 1.5 second time delay is implemented, allowing the bearings to settle before proceeding with the counterclockwise motion. After the completion of the 1.5 second delay, motor 125 will be caused to rotate in a counterwise direction for approximately 30 seconds. At the completion of the counterclockwise rotation, the control means will cause the door solenoid 192 to release latch arm 196 and bearing clamp 270 to release cartridge 230.

The control means for a particular tester 100 generally comprises individual test apparatus timing electronics, located on printed circuit board 180, and computer 400. A computer 400 for use with the present invention man comprise an Intel 80286 or 80386 based system, and it should be recognized that the microprocessor based controller component of the control means of the present invention need not be limited to Intel based systems.

Figure 9A:
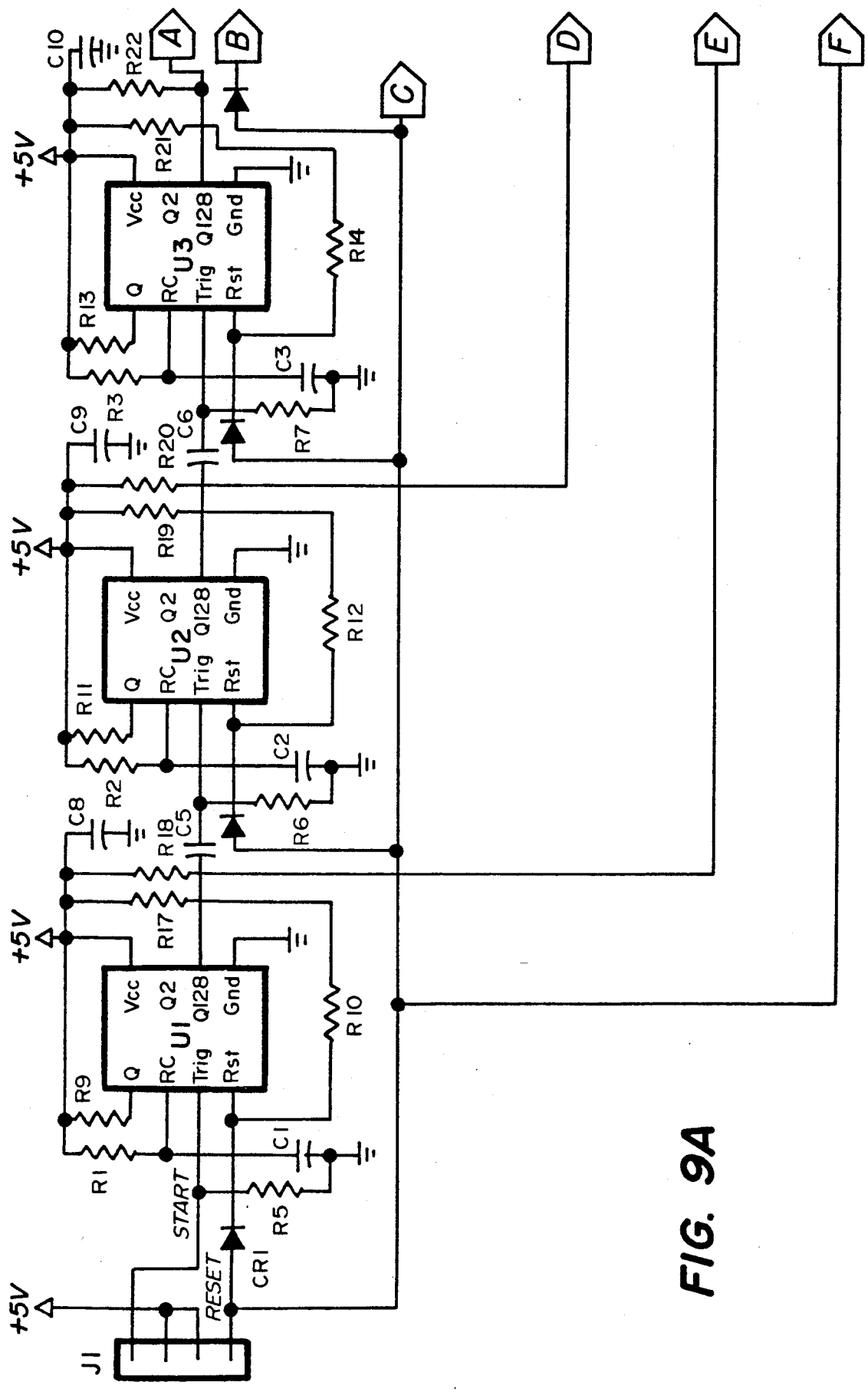
FIGS. 9A and 9B are a schematic diagram showing the configuration of the printed circuit board timing electronics of the apparatus of the present invention.
Figure 9B:
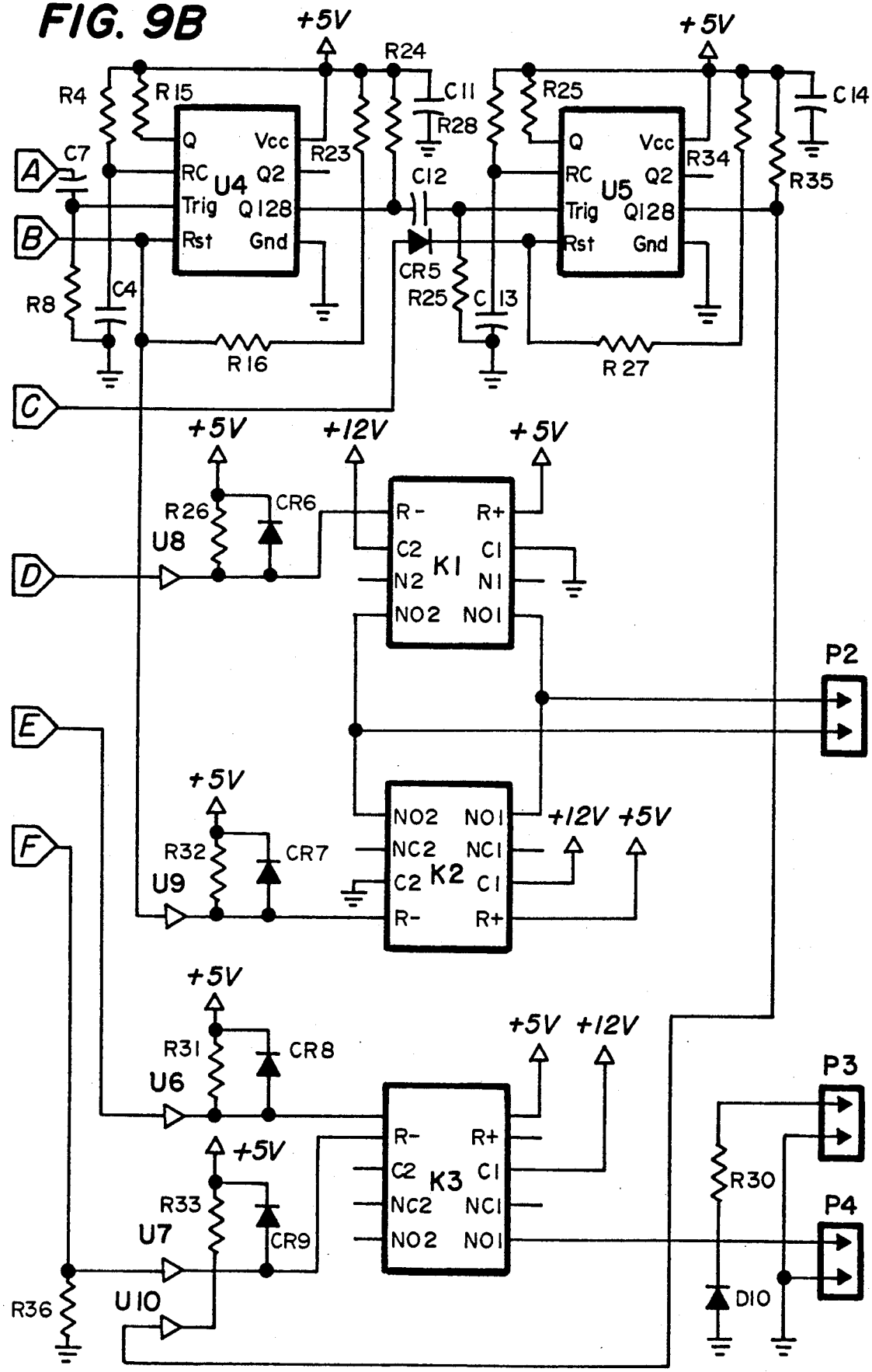

The specific aspects of the timing electronics will be described with respect to FIGS. 9A and 9B. FIGS. 9A and 9B are a schematic diagram of the timing circuitry located on PCB 180 utilized to control the various electromechanical components of bearing friction tester 100. Five analog timers U1-U5 control the electromechanical components of bearing friction tester 100. Each analog timer may comprise, for example, a model XR-2242 Long Range Timer manufactured by Exar Corporation. Each such analog timer is controlled by initiating a positive going trigger pulse to the TRIG input which enables a time base oscillator and sets the output Q128 to low. The time base oscillator generates timing pulses with the time period $T=RC$, and output Q128 maintains a low output signal for a duration of $128 \times RC$, before returning high. Resistors R1 and C1 control the period for chip U1; resistors R2 and C2 control the period for timer U2; resistors R3 and capacitor C3 control the period for timer U3; resistor R4 and capacitor C4 control the period for timer U4; and resistor R28 and capacitor C13 control the period for timer U5. As should be readily understood, any number of various timers may be utilized with equivalent efficiency.

Timers U1-U5 are coupled in a cascade fashion so that each preceding timer initiates the timing cycle for the next succeeding timer. The TRIG input of timer U1 is coupled to a switched, 5 volt input on connector P1. As shown in FIGS. 9 and 10, connector P1 couples to start switch 182 for enabling a 5 volt input pulse to the TRIG input of timer U1. The RESET input of each timer U1-U5 is coupled in parallel to a switched reset line which, as shown in FIG. 10, is controlled by shut-off switch 184. Switch 184 is also coupled to the RESET input of relay K3 which, as is discussed further below, disables latch solenoid 192 and air solenoid 290. As shown in FIGS. 9 and 10, the Q128 output of timer U1 is coupled via buffer U6 to the L- input of relay K3. The L+ and R+ inputs of relay K3 are coupled to +5 volt output of a 12 v/5 v DC power supply while the C1 input is coupled to the 12 volt output. The NO (normal open) outputs of relay K3 are coupled to connectors P3 and P4 which, as shown in FIG. 10, are coupled to a green indicator light 186, and latch solenoid 192 and air solenoid 290, respectively. When the Q128 output of timer U1, is driven LOW during the counting sequence of timer U1, relay K3 will couple the 12 volt input signal coupled to input C1 to the P3 and P4 outputs. Timer U1 thereby energizes green indicator light 186, signaling that the test procedure has commenced, and activates latching solenoid 192 and air solenoid 290 to trigger closure of latch pin 195 and clamp arm 270. The Q128 output of timer U1 provides a delay of approximately 1.5 seconds; to accomplish this, capacitor C1 has a value of approximately 10 μF and resistor R1 has a value of approximately 1.2 kΩ.

As noted above, the output Q128 of timer U1 is coupled to the TRIG input of timer U2 in a cascade type fashion. Timer U2 operates drive motor 125 for approximately 30 seconds, in one particular direction, allowing the balls and the particular bearings under test to make one rotation during the time period. As shown in FIG. 9, the Q128 output of timer U2 is coupled via buffer U8 to the R- input of relay K1. The C1 and C2 inputs of relay are coupled to ground and +12 volts, respectively, and the normal open (NO1, NO2) outputs of relay K1 are coupled to pin out P2. As will be seen in FIG. 10, connector P2 is coupled to motor 125. The 30 second running time for motor 125 is provided by resistor R2 which may have a value of 24 kΩ and capacitor C2 which may have a value of 10 μF. As will be generally understood, the Q128 output of timer U2 when held low for 30 seconds by timer U2, will cause relay K1 to couple the 12 V DC voltage and ground to pins 1 and 2 of connector P2 to drive motor 125.

Timer U3 is coupled to and triggered by the output Q128 of timer U2. Timer U3 provides a 1.5 second delay that allows for the bearing under test, and relays K1 and K2, both analog relays, to settle, while motor 125 prepares to switch direction. Timer U3 also allows bearing holder 230 to come to a neutral position where pins $232_1$ and $232_2$ are centered with respect to transducer substrate 204. To provide this 1.5 second delay, resistor R3, is provided with a value of 1.21 Ω capacitor C3 is provided with a value of 10 μF. The Q128 output of timer U3 will activate timer U4 on its rising edge.

Timer U4 has a TRIG input which is coupled to and triggered by the Q128 output of timer U3. Timer U4 enables motor 125 to rotate in the direction opposite that initiated by timer U2 for approximately 30 seconds. As shown in FIG. 9, the Q128 output of timer U4 is coupled via buffer U9 to the R- input of relay K2. As will be noted in FIG. 9, the C1 and C2 inputs of relay K2 are coupled to 12 V and ground, respectively, (thus having a polarity opposite to that corresponding on relay K1). Thus, the polarity of the normal open outputs (NO1, NO2) of relay K2 is opposite that of relay K1 and, when the Q128 output of timer U4 goes LOW, motor 125 rotates in a direction opposite to that generated by relay K1. Again, the duration of the Q128 output is 30 seconds, requiring a value of 24 kΩ on resistor R4 and 10 μF for resistor C4. As such, the Q128 outputs of timers U2 and U4 implement, respectively, the NO1 and NO2 outputs of relays K1 and K2 to provide current to motor 125, thereby driving motor 125 in a direction opposite to each other.

Output Q128 of timer U4 triggers the fifth stage timer U5 which releases the door latch solenoid 192 to allow latch finger 196 to be released. The Q128 output of timer U5 is coupled via buffer U10 to the R- input of relay K3. Once the output goes LOW, the relay K3 will be reset inhibiting the 12 volt output to couplings P3 and P4, and the NO1, NO2 outputs of relay K3 will return to their open positions. Resistor R 28 has a value of 1.21 kΩ and capacitor C13 has a value of 10 μF. As noted above, cover 170 may be springloaded such that when solenoid 192 raises pin 195, and latch 196 is released, cover 170 springs away from housing 142 and uncovers spindle 220.

Emergency shut-off/reset switch 184 is coupled to pins 1 and 2 of connector P1. Switch 184 couples a 5 volt power supply output to the reset (RST) inputs of timers U1, U2, U3, U4 and U5, and also to the R- input of relay K3 via inverter U7. Coupling the 5 volt signals of the reset inputs of the timers will reset the timing cycles thereof and the timers will remain dormant until the first rising edge signal engages timer U1. The LOW signal applied to the R- input of relay K3 via inverter U7 will reset relay K3 and the normal open (NO1) output thereof.

Figure 7A:
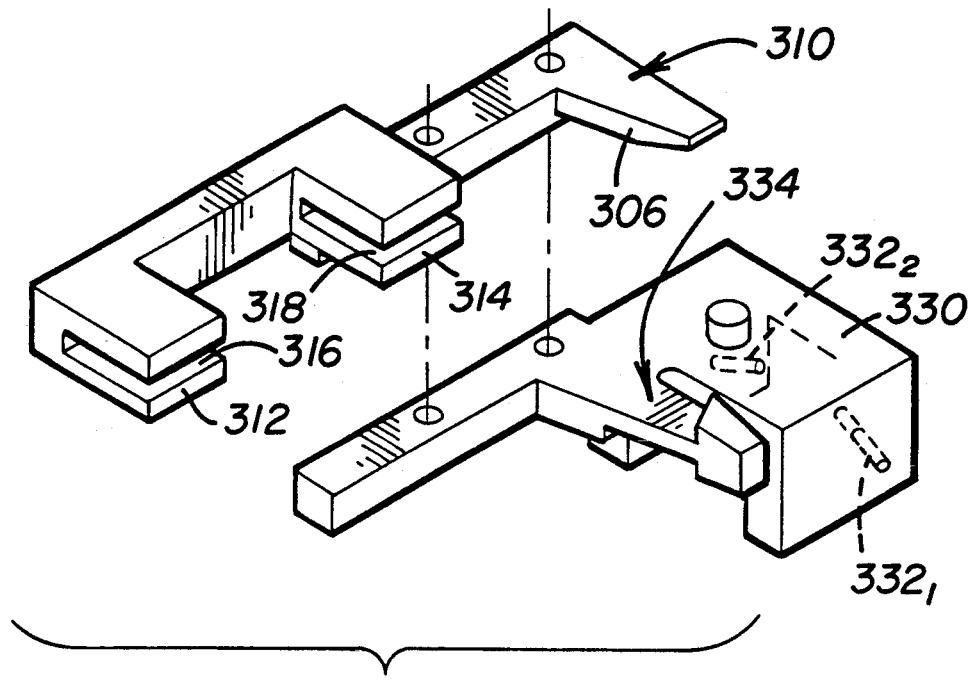
FIGS. 7A and 7B are perspective views of the disk drive actuator body adaptor for the apparatus of the present invention allowing the apparatus to test an assembled actuator bearing cartridge.
Figure 7B:
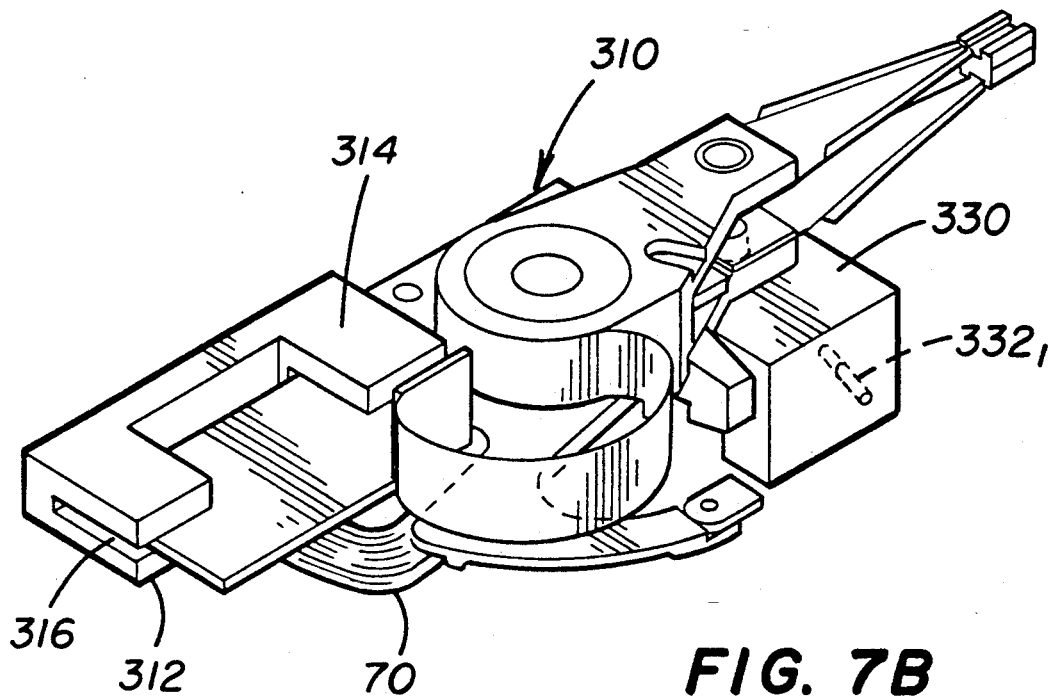

In FIGS. 1-6, bearing friction tester 100 of the present invention has been described with reference to testing of the bearing cartridge 40 independently of the actuator arm 52 utilized, for example, in the disk drive shown in FIG. 11. FIGS. 7A and 7B show an actuator arm attachment for allowing bearing cartridge 40 to be tested while mounted in actuator arm 52 of the disk drive shown in FIGS. 11A and 11B. As shown in FIG. 7A, main body 330 includes pins $332_1$ and $332_2$ which function to engage transducer load beam 204 in a like manner as pins $232_1$ and $232_2$ of bearing holder 230. Main body 330 also includes notch 334 for supporting subarm 52b of actuator arm 52. Bearing holder 330 further includes flex coil support assembly 310 including subarms 312 and 314 with slots 316 and 318 formed therein, respectively, for holding the flex circuit mounting plate in a secured relationship with respect to clamp 330. As shown in FIG. 7B, when the subarm holding assembly 310 is coupled to main body 330, arm 306 and notch 334 secure actuator subarm 52B, and actuator arm 52, in a rigid fashion. During the disk drive assembly operation, bearing cartridge 40 may be glued into actuator arm 52 before placement into the disk drive shown in FIG. 12. After such an operation, actuator holding clamp 330 may be utilized to test the bearing cartridge running friction while the bearing cartridge is mounted in the actuator via 52.

The bearing testing method and apparatus of the present invention thus provides a portable, modular testing system wherein each bearing test apparatus 100 may be operated as a single unit in a desktop or portable arrangement, or a multiplicity of testers may be operated in conjunction with a single personal computer controller. The apparatus is significantly smaller and more portable than prior art systems while determining bearing efficiency with a high degree of precision. In addition, provision is made for testing of bearings used in disk drives while the bearings are in a state of assembly into the actuator arms.

These and other features and advantages of the bearing testing method and apparatus in accordance with the present invention will be apparent to those of ordinary skill in the art from the foregoing description and the drawings. Further, the following claims are intended to cover all modifications and equivalents falling within the scope of the invention.

We claim:

1. A method for improving the reliability of manufactured disk drives, comprising:
   testing the bearing structures found within the disk drives by
   (a) measuring the running friction when the bearing is rotated in a counterclockwise direction;
   (b) measuring the running friction when the bearing is running in a clockwise direction, and
   (c) comparing each measurement prior to installing the bearing in a manufactured disk drive.

2. The method of claim 1 wherein, prior to step (a), the method further includes:
   coupling the outer race of the bearing to a strain gauge; and
   coupling the strain gauge to a full Wheatstone bridge arrangement.

3. The method of claim 2 wherein each said step (b) and (c) of measuring comprises:
   determining the force exerted on the load beam when the bearing is rotated by evaluating the voltage output of the Wheatstone bridge.

4. The method of claim 2 wherein the steps of measuring are performed automatically.

5. A method for testing bearings, the bearing having an inner race and an outer race, comprising:
   (a) coupling the outer race of the bearing to a strain gauge;

(b) rotating the inner race of the bearing in a first direction and measuring the torque exerted on the outer race; and (c) rotating the inner race of the bearing in a second direction and measuring the torque exerted on the outer race.

6. The method of claim 5 wherein said method includes coupling the load beam to a Wheatstone bridge prior to step (b).

7. The method of claim 5 wherein steps (b) and (c) are performed by an automated control means.

8. The method of claim 7 wherein the control means may control up to eight separate bearing tests simultaneously.

9. The method of claim 5 wherein said steps of rotating and measuring further include:

recording the magnitude of the torque measured versus time, and recording a maximum magnitude of the torque measured.

10. The method of claim 9 further including the step of:

comparing the maximum magnitude of the torque measured for each direction of rotation.

11. An apparatus for testing bearings, comprising:

means for moving a first race of the bearing in a first direction and a second direction relative to a second race;

a strain gauge;

means for coupling the outer race of the bearing to the strain gauge; and means, coupled to the strain gauge, for measuring the force applied to said strain gauge when said inner race is rotated; and means for clamping the bearing during testing, wherein said means for clamping may be positioned between an unclamped position and a clamped position.

12. The apparatus of claim 11 wherein said means for moving, said strain gauge, and said means for coupling are provided in a transportable arrangement.

13. The apparatus of claim 11 further including a signal conditioner, coupled to the output of the strain gauge, for coupling the output thereof to the means for measuring the force applied to the strain gauge.

14. The apparatus of claim 13 wherein said means for measuring includes a signal conditioner coupled to said strain gauge, and a computer, coupled to said signal conditioner.

15. The apparatus of claim 14 wherein the strain gauge includes a load beam and a Wheatstone bridge, and the signal conditioner is coupled to the Wheatstone bridge.

16. The apparatus of claim 15 wherein said apparatus further includes means for controlling said means for moving, wherein said means for controlling directs an automatic test sequence subsequent to the provision of the bearing under test to the apparatus.

17. The apparatus of claim 16 wherein said means for rotating comprises a spindle, coupled to a motor, said motor being responsive to said control means.

18. The apparatus of claim 17 wherein said means for controlling comprises timing circuitry coupled to said motor, and a computer coupled to the signal conditioner.

19. A method for measuring the running friction of a bearing, comprising:

coupling the outer race of a bearing to a strain gauge, the gauge including a load beam;

rotating the inner race of the bearing in a first direction and simultaneously measuring the force applied to the load beam by the outer race;

rotating the inner race of the bearing in a second direction and simultaneously measuring the force applied to the load beam by the outer race; and comparing the forces applied by the outer race to the load beam.

20. An apparatus for measuring the running friction of a bearing, the bearing having an inner race and an outer race, comprising:

a housing;

a spindle, mounted on the housing, having a central shaft and base, the shaft extending from the base and having a diameter sufficient to accommodate the inner race of a bearing under test;

a motor mounted under the housing for rotating the spindle;

a bearing holder, having a cylindrical bore of sufficient diameter to receive the outer race of a bearing under test;

a clamp, positioned adjacent the spindle, being rotatable between a first, unclamped position, and a second clamped position;

a load beam, positioned adjacent the spindle and in a position to engage the holder when the holder is mounted on a bearing and the bearing is mounted on the spindle, the load beam having a strain gauge at one end; and control means, coupled to said motor, clamp and load beam, for controlling the rotation of the spindle, and for measuring the force applied by the housing to the strain gauge when the spindle is rotated.

21. The apparatus of claim 20 further including an air solenoid, having an output shaft, the output shaft being coupled to the clamp.

22. The apparatus of claim 21 further including a signal conditioner coupled to the strain gauge, the load beam comprising a Wheatstone bridge.

23. The apparatus of claim 22 wherein said control means comprises:

a cascade timer, having selected outputs coupled to a plurality of switches, the switches for coupling a voltage to the motor, the air solenoid, and an indicator lamp, and a computer, having data inputs coupled to the signal conditioner and selected timer outputs.

24. An apparatus for improving the manufacturing yields in the production of hard disk drives, comprising:

means for rotating the inner race of the bearing with respect to the outer race; and means for detecting the running friction between the inner race of the bearing and the outer race of the bearing when the inner race is rotated in a clockwise direction and when the inner race is rotated in a counterclockwise direction, and for comparing the magnitude of the running friction of the bearing in the first direction and in the second direction to a specified friction.

* * * * *

UNITED STATES PATENT AND TRADEMARK OFFICE
CERTIFICATE OF CORRECTION

PATENT NO. : 5,311,763

DATED : May 17, 1994

INVENTOR(S) : Gibbs, Jr., et al.

It is certified that error appears in the above-identified patent and that said Letters Patent is hereby corrected as shown below:

Col. 1, line 24: "contract" should be "contact"

Col. 2, line 30: "a" should be "an"

Col. 2, line 38: "out" should be "outer"

Col. 2, line 59: "to provide a" should be "to provide an"

Col. 6, line 27: after "with" insert --air--

Col. 7, line 1: after "scale" insert a period

Col. 7, line 63: "compute" should be "computer"

Col. 8, line 35: "pin 146" should be "finger 146"

Col. 9, line 53: "counterwise" should be "counterclockwise"

Col. 11, line 13: before "capacitor" insert --and--

Col. 9, line 61: after "A computer 400" insert --suitable--

UNITED STATES PATENT AND TRADEMARK OFFICE
CERTIFICATE OF CORRECTION

PATENT NO. : 5,311,763

DATED : May 17, 1994

INVENTOR(S) : Gibbs, Jr., et al.

It is certified that error appears in the above-identified patent and that said Letters Patent is hereby corrected as shown below:

Col. 11, line 24: after "coupled to" insert --+--

Col. 12, line 19: delete "via"

Signed and Sealed this

Twenty-seventh Day of December, 1994

Attest:

BRUCE LEHMAN

*Attesting Officer*    *Commissioner of Patents and Trademarks*